United States Patent
Ataide Saraiva et al.

(10) Patent No.: US 12,383,537 B2
(45) Date of Patent: Aug. 12, 2025

(54) (3S)-AND (3R)-6,7-BIS(HYDROXYMETHYL)-1H,3H-PYRROLO[1,2-C]THIAZOLES AS P53 ACTIVATORS

(71) Applicants: UNIVERSIDADE DE COIMBRA, Coimbra (PT); UNIVERSIDADE DO PORTO, Oporto (PT)

(72) Inventors: Lucilia Helena Ataide Saraiva, Oporto (PT); Joana Oliveira Gama Soares, Oporto (PT); Teresa Margarida Vasconcelos Dias De Pinho E Melo, Coimbra (PT); Maria Isabel Lopes Soares, Coimbra (PT); Helena Isabel Nogueira Ramos Rocha, Oporto (PT)

(73) Assignees: UNIVERSIDADE DE COIMBRA, Coimbra (PT); UNIVERSIDADE DO PORTO, Oporto (PT)

(*) Notice: Subject to any disclaimer, the term of this patent is extended or adjusted under 35 U.S.C. 154(b) by 937 days.

(21) Appl. No.: 17/254,048

(22) PCT Filed: May 2, 2019

(86) PCT No.: PCT/IB2019/053603
§ 371 (c)(1),
(2) Date: Dec. 18, 2020

(87) PCT Pub. No.: WO2019/243906
PCT Pub. Date: Dec. 26, 2019

(65) Prior Publication Data
US 2021/0315866 A1 Oct. 14, 2021

(30) Foreign Application Priority Data
Jun. 20, 2018 (PT) .................................. 110795

(51) Int. Cl.
A61P 35/00 (2006.01)
A61K 31/429 (2006.01)
A61K 45/06 (2006.01)
C07D 513/04 (2006.01)

(52) U.S. Cl.
CPC ............ *A61K 31/429* (2013.01); *A61K 45/06* (2013.01); *A61P 35/00* (2018.01); *C07D 513/04* (2013.01)

(58) Field of Classification Search
CPC ...... A61K 31/429; A61P 35/00; C07D 513/04
See application file for complete search history.

(56) References Cited

U.S. PATENT DOCUMENTS

2016/0101150 A1* 4/2016 Jaynes .................... A61K 38/16
514/21.7

FOREIGN PATENT DOCUMENTS

EP 3013833 B1 3/2019

OTHER PUBLICATIONS

Santos et al. Targeting triple-negative breast cancer cells with 6,7-bis(hydroxymethyl)-1H,3H-pyrrolo[1,2-c]thiazoles, European Journal of Medical Chemistry 79 (2014) pp. 2743-281, Apr. 2014 [online], [retrieved on Oct. 12, 2023]. Retrieved from the internet < URL: Targeting triple-negative breast (Year: 2014).*
Soares et al. Chiral 6-hydroxymethyl-1H,3H-pyrrolo[1,2-c]thiazoles: Novel antitumor DNA monoalkylating agents, European Journal of Medical Chemistry 45 (2010) pp. 4676-4681, Jul. 2010 [online], [retrieved on Oct. 16, 2023]. Retrieved from the internet < URL: Chiral 6-hydroxymethyl-1H,3H-pyrrolo[1,2-c]t (Year: 2010).*
Soares et al. Chiral 6-hydroxymethyl-1H,3H-pyrrolo[1,2-c]thiazoles: Novel antitumor DNA monoalkylating agents, European Journal of Medical Chemistry 45 (2010) pp. 4676-4681, Jul. 2010 (Year: 2010).*
Soares et al. Chiral 6,7-bis(hydroxymethyl)-1H,3H-pyrrolo[1,2-c]thiazoles with anti-breast cancer properties, European Journal of Medical Chemistry 60 (2013) pp. 254-262, Nov. 2012. (Year: 2013).*
Soares et al. Chiral 6,7-bis(hydroxymethyl)-1H,3H-pyrrolo[1,2-c]thiazoles with anti-breast cancer properties, European Journal of Medical Chemistry 60 (2013) pp. 254-262, Nov. 2012. (Year: 2012).*
Santos et al., "Targeting triple-negative breast cancer cells with 6,7-bis(hydroxymethyl)-1H,3H-pyrrolo[1,2-c] thiazoles", European Journal of Medicinal Chemistry, 2014, vol. 79, pp. 273-281.
Soares et al., "Chiral 6,7-bis(hydroxymethyl)-1H,3H-pyrrolo[1,2-c]thiazoles with anti-breast cancer properties", European Journal of Medicinal Chemistry, 2013, vol. 60, pp. 254-262.

(Continued)

*Primary Examiner* — Sarah Pihonak
*Assistant Examiner* — Mikhail O'Donnel Robinson
(74) *Attorney, Agent, or Firm* — Lucas & Mercanti, LLP (57) ABSTRACT

The present application relates to compounds of formula I, which are (3S)- and (3R)-6,7-bis(Hydroxymethyl)-1H,3H-pyrrolo[1,2-c]thiazoles. The present application also relates to pharmaceutical compositions having the compounds and the use of these compounds in the treatment of conditions influenced by wild-type or mutant p53 forms. More specifically, these compounds represent a completely new chemical family of p53-activating agents and show a higher selectivity towards the p53-pathway compared to the reactivators of p53 currently under clinical trials. For some cancer types these compounds revealed to be more potent than the reactivators of p53 currently under clinical trials. In addition to these advantages, the presently disclosed compounds are not genotoxic and have no apparent undesirable toxic side effects.

9 Claims, 5 Drawing Sheets

(56) References Cited

OTHER PUBLICATIONS

Soares et al., "Chiral 6-hydroxymethyl-1H,3H-pyrrolo[1,2-c]thiazoles: Novel antitumor DNA monoalkylating agents", European Journal of Medicinal Chemistry, 2010, vol. 45, No. 10, pp. 4676-4681.
Ahmed et al., "Epigenetic and genetic features of 24 colon cancer cell lines", ONCOGENESIS, 2013, vol. 2, No. 9, pp. 1-8.
Peltonen et al., "Identification of novel p53 pathway activating small-molecule compounds reveals unexpected similarities with known therapeutic agents", PLOS ONE, 2010, vol. 5, Issue 9, pp. 1-12.
International Search Report and Written Opinion for Corresponding International Application No. PCT/IB2019/053603 (11 Pages) (Aug. 26, 2019).

* cited by examiner

(3S)- AND (3R)-6,7-BIS(HYDROXYMETHYL)-1H,3H-PYRROLO[1,2-C]THIAZOLES AS P53 ACTIVATORS

CROSS-REFERENCE TO RELATED APPLICATIONS

This application is a 371 of PCT/IB2019/053603, filed May 2, 2019, which claims the benefit of Portuguese Patent Application No. 110795, filed Jun. 20, 2018, each of which are incorporated herein by reference.

TECHNICAL FIELD

The present application relates to compounds (3S)- and (3R)-6,7-bis(Hydroxymethyl)-1H, 3H-pyrrolo[1,2-c]thiazoles, pharmaceutical compositions comprising said compounds and uses thereof.

BACKGROUND ART

A significant portion of anticancer drug development is currently focused on targeted therapies, which constitute the foundation of precision medicine. Targeted therapies differ from standard/conventional chemotherapy namely by acting on specific molecular targets associated with cancer, whereas most standard chemotherapies act on all rapidly dividing normal and cancerous cells, inducing cell death by nonspecific ways. These advantages translate into reduced toxicity to normal cells and less side effects for the patients (Chessum et al, Prog Med Chem 2015, 54:1-63). The tumor suppressor p53 is the most commonly inactivated protein in human cancers. In fact, the impairment of p53 as a signature of human cancer has long been recognized. The p53 protein functions as a sequence-specific transcription factor, initiating a cascade of cellular responses in order to prevent the replication of damaged DNA or the proliferation of genetically altered cells that can lead to tumor formation. Depending on the extension and severity of the stress stimulus and on the cell/tissue context, p53 may trigger a variety of cellular responses, including cell cycle arrest, DNA repair, senescence, apoptosis, and metabolic reprogramming. Therefore, targeting this protein for its activation represents one of the most reliable approach for cancer prevention and treatment (Essmann and Schulze-Osthoff, Br J Pharmacol 2012, 165:328-44; Sobol et al, p53 in the Clinics 2013, Springer, New York). Specifically, about half of the cancer patients have mutations in the TP53 gene. In fact, TP53 is the most frequently mutated gene in human cancers (Sabapathy and Lane, Nat Rev Clin Oncol 2018, 15:13-30). Despite the diversity of p53 mutations in tumors, most are missense mutations in the DNA-binding domain that result in deficient DNA binding and failure to transactivate target genes (loss-of-function). Even in tumors that still bear one wild-type p53 allele, the mutant form can exert a dominant negative effect over wild-type p53. Additionally, it has been reported that some mutant p53 may acquire new oncogenic properties, called gain-of-function (GOF), through transactivation of genes related to oncogenesis and aggressive tumor phenotypes or by inhibition, through heteroligomerization, of other transcription factors such as p63/p73 (Duffy et al, Eur J Cancer 2017, 83:258-265; Sabapathy and Lane, Nat Rev Clin Oncol 2018, 15:13-30). As such, mutant p53 has high clinical relevance since it is usually associated with poor prognosis, particularly with more resistant and metastatic tumor phenotypes (Duffy et al, Eur J Cancer 2017, 83:258-265; Sabapathy and Lane, Nat Rev Clin Oncol 2018, 15:13-30). In addition, since mutant p53 expression is generally restricted to tumor tissue, mutant p53-targeted therapies are expected to be highly selective. Finally, most conventional chemotherapeutic drugs function by inducing extensive DNA damage, therefore relying on a functional p53 pathway to lead to cell death. By restoring this pathway in mutant p53-expressing tumors, it may be possible to sensitize these highly chemoresistant cells to conventional chemotherapeutics, supporting the potential of mutant p53 reactivators in combination therapy (Duffy et al, Eur J Cancer 2017, 83:258-265; Sabapathy and Lane, Nat Rev Clin Oncol 2018, 15:13-30).

As such, many efforts have been focused on targeting mutant p53 as a therapeutic strategy to halt cancer. Indeed, to date, several new chemical entities have been reported with the ability to restore wild-type-like function to mutant p53 (called reactivation), with PRIMA-1MET, COTI-2, PEITC, WR-1065, and aminoglycosides reaching clinical trials. However, for some of them, such as COTI-2, off-target effects have been reported. Moreover, toxic side effects have also been reported for reactivators of mutant p53. This can justify that, to date, no p53 activators can be found in the clinic (Duffy et al, Eur J Cancer 2017, 83:258-265; Sabapathy and Lane, Nat Rev Clin Oncol 2018, 15:13-30). In addition to these major concerns, the ability of these small molecules to reactivate multiple mutant p53 forms remains unclear and a major pharmacological challenge, which needs to be addressed to reach a broader population of patients with mutant p53-related cancers (Duffy et al, Eur J Cancer 2017, 83:258-265; Sabapathy and Lane, Nat Rev Clin Oncol 2018, 15:13-30).

Collectively, despite the existence of small molecule p53 activators in early phases of clinical trials, none has been approved for clinical use. Given the recognized relevance of p53 activation to the effectiveness of anticancer therapy, new p53 activators are required to be used as single agents or in combination therapy.

Document EP3013833 discloses a novel family of Tryptophanol-Derived Oxazoloisoindolinones for use in the treatment of p53-associated conditions, such as cancer. These compounds are p53 activators and may be used in pharmaceutical compositions, alone or in combination with other chemoterapeutic agents. The present application differs from the disclosed technology since it relates to pyrrolothiazole molecules as an alternative to already existing p53 activators.

In 2013, Soares et al. reported the synthesis and biological evaluation of chiral 6,7-bis(hydroxymethyl)-1H,3H-pyrrolo[1,2-c]thiazoles as promising scaffold for the design of new anticancer compounds against breast cancer cells. Among the synthesized molecules (3S)- and (3R)-6,7-bis (hydroxymethyl)-5-methyl-3-phenyl-1H, 3H-pyrrolo[1,2-c]thiazoles showed potent anti-proliferative activity against MCF7 breast cancer cell lines (Soares et al, Eur J Med Chem 2013, 60:254-262). In a subsequent publication (Santos et al, Eur J Med Chem 2014, 79:273-281), only the activity of (3R)-6,7-bis(hydroxymethyl)-5-methyl-3-phenyl-1H,3H-pyrrolo[1,2-c]thiazole enantiomer was explored in breast cancer cells. However, the marked cell death induced by (3R)-6,7-bis (hydroxymethyl)-5-methyl-3-phenyl-1H,3H-pyrrolo[1,2-c]thiazole in breast cancer cells was not related to the p53 pathway. In fact, in both publications, no assumptions about the molecular mechanism of action of (3S)- and (3R)-6,7-bis(hydroxymethyl)-5-methyl-3-phenyl-1H,3H-pyrrolo[1,2-c]thiazoles were made.

SUMMARY

The present application relates to compounds, or pharmaceutically acceptable salts, of formula (I), (I)

wherein,
R$^1$=H, alkyl, aryl, aroyl or heteroaryl;
R$^2$=H, alkyl, aryl, aroyl or heteroaryl;
R$^3$=H, alkyl or aryl,
for use in the treatment of conditions associated with wild-type or mutant p53 forms.

In one embodiment the conditions associated with wild-type or mutant p53 forms are cancers.

In another embodiment the cancers are colorectal cancers.

In yet another embodiment the conditions are skin, lung, and liver cancers.

The present application also discloses compounds for use as chemoprotectants.

In yet another embodiment, the present application relates to a pharmaceutical composition comprising a therapeutically effective amount of the compound described herein and further comprising a pharmaceutically effective carrier.

In one embodiment the pharmaceutical composition further comprises a chemotherapeutic agent.

In one embodiment the pharmaceutical composition is for use in the treatment of cancers associated with wild-type or mutant p53 forms.

In another embodiment the pharmaceutical composition is for use in colorectal, skin, lung, and liver cancers.

In yet another embodiment the pharmaceutical composition is for use as a chemoprotectant.

In one embodiment the pharmaceutical composition is administered via topical, oral, parenteral or injectable route.

General Description

The present application provides a completely different chemical structure of p53 activators from those described so far, the compounds (3S)-(also known as MANIO) and (3R)-6,7-bis(hydroxymethyl)-1H,3H-pyrrolo[1,2-c]thiazoles, with the ability to target both wild-type and mutant p53 forms.

When compared to (3R)-6,7-bis(hydroxymethyl)-5-methyl-3-phenyl-1H,3H-pyrrolo[1,2-c]thiazole, the enantiomer (3S)-6,7-bis(hydroxymethyl)-5-methyl-3-phenyl-1H,3H-pyrrolo[1,2-c]thiazole (MANIO) revealed higher selectivity to the p53 pathway and antitumor activity, particularly against colon cancer cells.

MANIO displays potent antitumor activity both in human cancer cells and animal xenograft mice models. Additionally, MANIO has high selectivity to the p53-pathway, absence of genotoxicity and no apparent toxic side effects. Altogether, these properties make this compound a superior molecular probe and anticancer drug candidate compared to other p53-activating agents currently available. Most importantly, its ability to reactivate a broad panel of mutant p53 forms with high prevalence may predict promising clinical applications of MANIO in the personalized therapy of a wide range of cancer patients. Collectively, possible benefits that this technology may provide for the pharmaceutical market of anticancer agents include: i) an improvement of the anticancer therapy, as well as of patient's quality of life, by using a more effective and selective chemical agent, without the undesirable toxic side effects commonly associated with cancer treatments; ii) the possibility of expanding the population of cancer patients that may benefit from cancer treatments by using a small molecule that may target both wild-type and a broad panel of highly prevalent mutant p53 forms; iii) a potential reduction of the costs commonly associated with p53-activating agents and anticancer agents by using a small molecule obtained using simplified processes of synthesis, suitable for scale-up with high yields and purity.

The small molecule MANIO can be used as a chemical probe in the cancer research field to study the wild-type and mutant p53 signaling pathway. Additionally, a formulation containing this compound as active component may be an effective strategy to prevent and treat cancer with an impaired p53 pathway. Therefore, the oncology sector, including both the fine chemical industry and the pharmaceutical companies, are the major market sectors with potential interest in this technology.

The presently disclosed compounds have the following features:
- Represent a completely new chemical family of p53-activating agents;
- Present a higher selectivity towards the p53-pathway compared to the reactivators of p53 currently under clinical trials;
- For some cancer types, particularly colorectal cancers, these compounds reveal to be more potent than the reactivators of p53 currently under clinical trials;
- These compounds are not genotoxic and have no apparent undesirable toxic side effects.

BRIEF DESCRIPTION OF DRAWINGS

The present invention is illustrated by way of example, and not by way of limitation, in the figures of the accompanying drawings and in which like reference numerals refer to similar elements and in which:

FIG. 6 illustrates the MANIO effect on protein levels of p53 (A), the mRNA (B) and protein (C) expression levels of p53 target genes and PARP cleavage, in HCT116 p53+/+ and HCT116 p53−/− cells. (B) mRNA levels of p53 target genes in HCT116 cells (MDM2, CDKN1A, GADD45A, BAX, TNFRSF10B, PUMA, NOXA), after 48 hours treatment with MANIO, or DMSO, determined by RT-qPCR. Fold of induction is relative to DMSO. Data are mean±SEM (n=3; values significantly different from DMSO: *p<0.05; p<0.01; *p<0.001; two-way ANOVA with Dunnett's multiple comparison test) Protein expression was analysed by Western blot, and results correspond to: (A) 24, 48, and 72 hours treatment with 1 μM MANIO for p53; (B) 48 hours (for MDM2, p21, and GADD45) and 72 hours (for PARP, BCL-2, KILLER, and PUMA) treatment with 1 μM MANIO. Immunoblots represent one of three independent experiments. GAPDH was used as a loading control.

FIG. 10 illustrates the in vivo antitumor activity of MANIO. (A) Swiss nude mice were implanted subcutaneous with xenografts of 1.5×106 HCT116 p53+/+ cells. The treatment was initiated when palpable tumors were established (~100 mm3) and consisted in 4 intraperitoneal injections (2 times per week) of vehicle (control) or 100 mg/kg of MANIO (n=5 for each group). Relative tumor volumes were plotted for control and treated groups by dividing the tumor volume for each data point by starting tumor volume; values significantly different from control mice (*p<0.05, **p<0.01; unpaired Student's t-test). (B) The tumor weight after MANIO or vehicle (control) treatment was measured; data are mean±SEM (*p<0.05; unpaired Student's t-test). (C) Mice were weighted during MANIO or vehicle (control) treatment; no significant differences between control and MANIO-treated mice weight (p>0.05; unpaired Student's t-test). This description is of course not in any way restricted to the forms of implementation presented herein and any person with an average knowledge of the area can provide many possibilities for modification thereof without departing from the general idea as defined by the claims. The preferred forms of implementation described above can obviously be combined with each other. The following claims further define the preferred forms of implementation.

DESCRIPTION OF EMBODIMENTS

Now, preferred embodiments of the present application will be described in detail with reference to the annexed drawings. However, they are not intended to limit the scope of this application.

The present application discloses selective activators of wild-type and mutant forms of p53, the 6,7-bis(hydroxymethyl)-1H,3H-pyrrolo[1,2-c]thiazoles with general formula (1), wherein:
R$^1$=H, alkyl, aryl, aroyl or heteroaryl;
R$^2$=H, alkyl, aryl, aroyl or heteroaryl;
R$^3$=H, alkyl or aryl
Wherein the 3S enantiomer is represented by:
R$^1$=H;
R$^2$=alkyl, aryl, aroyl or heteroaryl;
R$^3$=H, alkyl or aryl
And the 3R enantiomer is represented by:
R$^1$=alkyl, aryl, aroyl or heteroaryl;
R$^2$=H;
R$^3$=H, alkyl or aryl The term "alkyl" is used herein to denote a methyl or ethyl group.

The term "aryl" is used herein is any carbon-based aromatic group including, but not limited to, benzene, naphthalene, etc. The aryl group can be substituted with one or more groups including, but not limited to, alkyl, halide, nitro, amino, hydroxyl, carboxylic acid, or alkoxy.

The term "heteroaryl" is used herein to denote an aryl group in which said group comprises at least one heteroatom, selected from nitrogen, oxygen and sulfur.

The term "aroyl" is used herein to denote an aryl carbonyl group.

The compounds (3S)- and (3R)-6,7-bis(hydroxymethyl)-1H,3H-pyrrolo[1,2-c]thiazoles can be used as molecular probe in p53 research field, as chemopreventive, suppressing tumor formation, or as chemotherapeutic, suppressing tumor progression and dissemination of several cancer types, including colorectal, skin, lung, and liver cancers. These compounds, or their pharmaceutically acceptable salts, represent a completely new chemical family of p53-activating agents, with high selectivity towards the p53-pathway and high potency as anticancer agent. Additionally, the presently disclosed compounds have no genotoxicity or apparent undesirable toxic side effects. Finally, they have a simplified and a low-cost synthesis. Altogether, this technology will allow improving anticancer therapy and patient's quality of life, and to expand the population of cancer patients that may benefit from cancer treatments. Additionally, the use of these compounds will contribute to a reduction in the costs associated with p53 cancer research and cancer treatment.

In a preferred embodiment the (3S)-6,7-bis(hydroxymethyl)-1H,3H-pyrrolo[1,2-c]thiazoles is used for the treatment of conditions associated with wild-type or mutant p53 forms. In one embodiment, the present application also relates to pharmaceutical compositions comprising therapeutically effective amount of the compounds described herein and further comprising a pharmaceutically effective carrier. In another embodiment, the pharmaceutical compositions further comprise a chemotherapeutic agent.

The compounds of the present application, of the pharmaceutical compositions comprising the compounds, can also be used as chemoprotectants.

The compounds of the present application, or the pharmaceutical compositions comprising them, are administered via topical, oral, parenteral or injectable route.

Preparation of Chiral 6,7-bis (hydroxymethyl)-1H, 3H-pyrrolo[1,2-c]thiazole

Chiral 6,7-bis(hydroxymethyl)-1H,3H-pyrrolo[1,2-c]thiazole (5) with S configuration was prepared as outlined in Scheme 1. The reaction of 2-phenylthiazolidine-4-carboxylic acid (2) with acetyl chloride in dry pyridine allow the exclusive formation of (2S,4R)—N-acetyl-2-phenyl-1,3-thiazolidine-4-carboxylic acid (3). Thiazolidine (3) reacts with dimethyl acetylene dicarboxylate in refluxing acetic anhydride to afford (3S)-1H,3H-pyrrolo[1,2-c]thiazole-6,7-dicarboxylate (4) which was converted into chiral 6,7-bis(hydroxymethyl)-1H,3H-pyrrolo[1,2-c]thiazole (5) upon reaction with lithium aluminium hydride.

Preparation of Chiral 6,7-bis (hydroxymethyl)-1H, 3H-pyrrolo[1,2-c]thiazol

Chiral 6,7-bis (hydroxymethyl)-1H, 3H-pyrrolo[1,2-c]thiazole (7) with R configuration was prepared as outlined in Scheme 2. The reaction of 2-phenylthiazolidine-4-carboxylic acid (2) in refluxing acetic anhydride in the presence of dimethyl acetylene dicarboxylate affords 1H,3H-pyrrolo[1,2-c]thiazole-6,7-dicarboxylate (6) as single enantiomer with R configuration. Reduction of (6) with lithium aluminium hydride afforded 6,7-bis(hydroxymethyl)-1H,3H-pyrrolo[1,2-c]thiazole (7).

General Procedure for the Synthesis of 1H,3H-pyrrolo[1,2-c]thiazole-6,7-dicarboxylates A solution of the appropriate thiazolidine-4-carboxylic acid (18 mmol), dimethyl acetylene dicarboxylate (1.5 equiv., 27 mmol) and Ac2O (60 mL) was heated at 110° C. during the 4 h. The reaction was cooled to room temperature and was diluted with CH2Cl2 (150 mL). The organic phase was washed with saturated aqueous solution of NaHCO3 and with water, dried (Na2SO4) and evaporated off. The crude product was purified by flash chromatography [hexane-ethyl acetate] or recrystallisation.

Dimethyl (3S)-3-phenyl-5-methyl-1H,3H-pyrrolo[1,2-c]thiazole-6,7-dicarboxylate (4). The starting material was (2S,4R)-3-acetyl-2-phenylthiazolidine-4-carboxylic acid (3). Yield: 79%, white solid, mp 160-162° C. (from ethyl acetate-hexane). IR (KBr) 1729, 1705, 1450, 1340, 1292, 1154, 1095 cm-1. 1H NMR (400 MHz, CDCl3) δ 2.01 (s, 3H), 3.82 (s, 3H), 3.83 (s, 3H), 4.32 (d, J=14.9 Hz, 1H), 4.48 (d, J=14.9 Hz, 1H), 6.28 (s, 1H, CHPh), 7.05-7.07 (m, 2H, ArH), 7.33-7.35 (m, 3H, ArH). 13C NMR (100 MHz, CDCl3) δ 14.5, 30.0, 51.4, 51.6, 65.0, 106.8, 117.4, 125.6, 129.0, 129.3, 130.7, 140.1, 140.5, 164.0, 165.3. HRMS (EI-TOF) m/z 331.0877 (M+, C17H17NO4S requires 331.0878). $[\alpha]\_20^{\circ}D$=-175 (c 1, CH2Cl2).

Dimethyl (3R)-3-phenyl-5-methyl-1H, 3H-pyrrolo [1,2-c]thiazole-6,7-dicarboxylate (6) [1][2]

The starting material was 2-phenylthiazolidine-4-carboxylic acid (2). Yield: 75%, white solid, mp 149-151° C. (from ethyl acetate-hexane). 1H NMR (400 MHz, CDCl3) δ 2.01 (s, 3H), 3.83 (s, 3H), 3.84 (s, 3H), 4.32 (d, J=15.0 Hz, 1H), 4.48 (dd, J=15.0 and 1.7 Hz, 1H), 6.28 (d, J=1.7 Hz, 1H, CHPh), 7.04-7.07 (m, 2H, ArH), 7.32-7.37 (m, 3H, ArH). 13C NMR (100 MHz, CDCl3) δ 11.4, 30.0, 51.4, 51.6, 64.9, 106.8, 117.4, 125.6, 129.0, 129.3, 130.8, 140.1, 140.5, 164.0, 165.3. Found; C, 61.2; H, 5.2; N, 3.9. Calcd for C17H17N04S C, 61.6; H, 5.2; N, 4.6. $[\alpha]\_20^{\circ}D$=+160 (c 1, CHCl3).

General procedure for the synthesis of 6,7-bis(hydroxymethyl)-1H,3H-pyrrolo[1,2-c]thiazoles: A solution containing the appropriate 1H,3H-pyrrolo[1,2-c]thiazole (3.18 mmol) in dry dichloromethane (34 mL) was added dropwise to a suspension of lithium aluminium hydride (2.2 equiv., 7.00 mmol, 0.28 g) in anhydrous diethyl ether (48 mL) at 0° C. The solution was refluxed for 1.5 h after the addition was completed and then cooled on an ice bath. The excess of hydride was carefully decomposed by addition of ethyl acetate followed by slow addition of water (0.3 mL), NaOH 15% (0.3 mL) and water (0.9 mL). The mixture was filtered through celite and the inorganic residue was washed with several portions of hot dichloromethane. The filtrate was dried ($Na_2SO_4$) and the solvent evaporated off. The crude product was purified by flash chromatography [hexane-ethyl acetate] or recrystallisation.

(3S)-6,7-Bis(hydroxymethyl)-5-methyl-3-phenyl-1H,3H-pyrrolo[1,2-c]thiazole (5). Yield: 56%, white solid, mp 88-90° C. (from ethyl acetate-diethyl ether). IR (KBr) 3385, 1540, 1456, 1437, 1344, 1035, 1005 cm-1. 1H NMR (400 MHz, CDCl3) δ 1.84 (s, 3H), 2.82 (br s, 2H), 4.07 (d, J=12.8 Hz, 1H), 4.28 (d, J=12.8 Hz, 1H), 4.47 (d, J=12.3 Hz, 1H), 4.51 (d, J=12.0 Hz, 1H), 4.57 (s, 2H), 6.22 (s, 1H), 7.04-7.06 (m, 2H, ArH), 7.26-7.33 (m, 3H, ArH). 13C NMR (100 MHz, CDCl3) δ 10.0, 27.7, 56.4, 56.7, 64.4, 113.4, 123.0, 123.5, 125.7, 128.5, 129.0, 131.5, 141.6. HRMS (EI-TOF) m/z 275.0979 (M+, C15H17NO2S requires 275.0980). $[\alpha]\_20^{\circ}D$=-275 (c 1, CH2Cl2).

(3R)-6,7-Bis (hydroxymethyl)-5-methyl-3-phenyl-1H, 3H-pyrrolo[1,2-c]thiazole (7). Yield: 45%, white solid, mp 91-93° C. (from ethyl acetate-diethyl ether). IR (KBr) 3385, 1455, 1359, 1035, 1005 cm-1. 1H NMR (400 MHz, CDCl3) δ 1.83 (s, 3H), 3.13 (br s, 1H), 3.28 (br s, 1H), 4.06 (d, J=12.8 Hz, 1H), 4.27 (d, J=12.8 Hz, 1H), 4.44 (d, J=12.0 Hz, 1H), 4.48 (d, J=12.0 Hz, 1H), 4.54 (bs, 2H), 6.22 (s, 1H), 7.03-7.05 (m, 2H, ArH), 7.27-7.30 (m, 3H, ArH). 13C NMR (100 MHz, CDCl3) δ 9.9, 27.6, 56.2, 56.5, 64.3, 113.4, 123.0, 123.5, 125.7, 128.5, 129.0, 131.5, 141.6. HRMS (EI-TOF) m/z 275.0991 (M+, C15H17NO2S requires 275.0980). $[\alpha]\_20^{\circ}D$=+255 (c 1, CH2Cl2).

Biological Experiments

Figure 1:
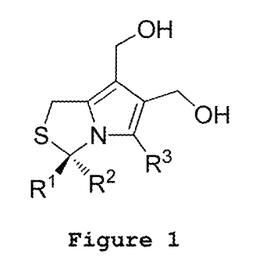
FIG. 1 shows the general structure of (3S)-(MANIO) and (3R)-6,7-bis (hydroxymethyl)-1H, 3H-pyrrolo[1,2-c]thiazoles.
Figure 2:
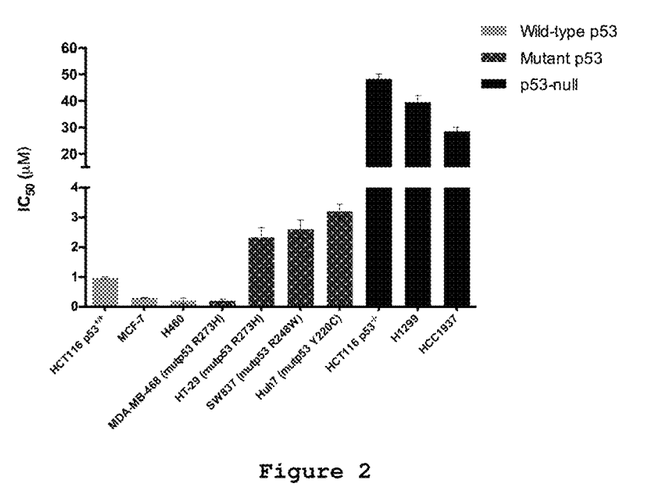
FIG. 2 illustrates the growth inhibitory effect of MANIO in a panel of human cancer cell lines (HCT116 p53+/+, MCF7, H460, MDA-MB-468, HT-29, SW837, Huh-7, HCT116 p53−/−, H1299, HCC1937). IC50 values were determined by the sulforhodamine B assay after 48 hours treatment with MANIO. Data are mean±SEM (n=4-5).

The compound (3S)-6,7-bis(hydroxymethyl)-1H,3H-pyrrolo[1,2-c]thiazole, MANIO, inhibited the growth of tumor cells expressing wild-type and mutant p53 forms, with much lower anti-proliferative effect on p53-null cancer cells: The activity of the compound (FIG. 1, with $R^1$=H, $R^2$=Ph and $R^3$=Me) was tested in an array of cancer cell lines with different p53 status. The $IC_{50}$ (concentration of compound that causes 50% growth inhibition) values of the compound ranged from 0.20-0.96 µM in wild-type p53-expressing cancer cells (colon HCT116 p53+/+, breast MCF7, and lung H460 cells), 0.20-3.20 µM in mutant p53-expressing cancer cells (breast MDA-MB-468, rectum SW837, colon HT29, and hepatocarcinoma Huh-7 cells), and 28.50-48.25 µM in p53-null cancer cells (colon HCT116 p53-/-, breast H1299 and HCC1937 cells) (FIG. 2). The results obtained showed a promising antitumor activity of the compound against distinct types of cancer, including colon, rectum, breast, lung, and liver cancers. Moreover, the IC50 values of the compound are significantly higher in p53-null cancer cells when compared to wild-type or mutant p53-expressing cancer cells, which corroborates the p53-dependent anti-proliferative activity of the compound.

Figure 3:
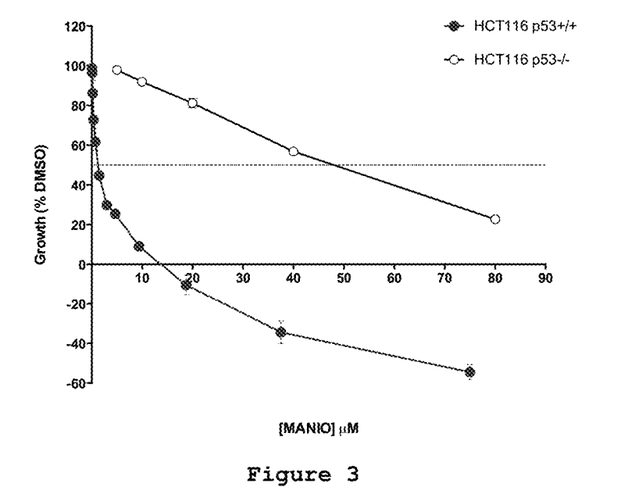
FIG. 3 illustrates the concentration-response curves for the growth inhibitory effect of MANIO on colon adenocarcinoma HCT116 p53+/+ and HCT116 p53−/− cells, determined by the sulforhodamine B assay after 48 hours treatment. Data are mean±SEM (n=4-5).
Figure 4:
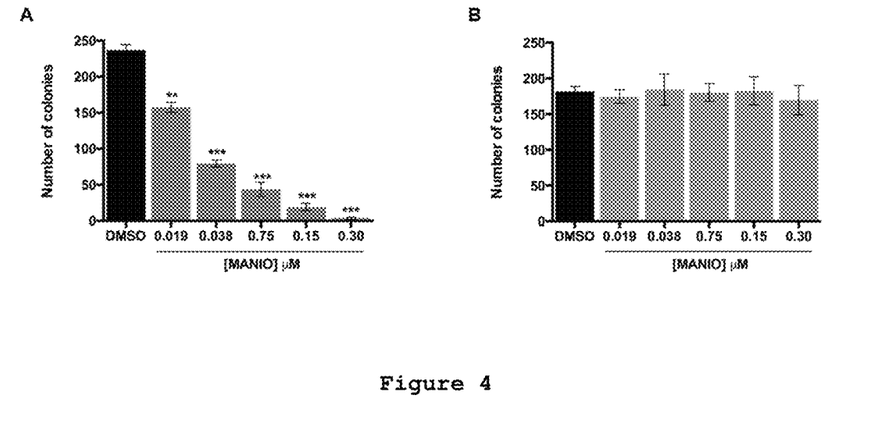
FIG. 4 illustrates the effect of MANIO on HCT116 p53+/+ (A) and HCT116 p53−/− (B) cell colony formation after 14 days of treatment. Data are mean±SEM (n=4; values significantly different from DMSO: p<0.01; *p<0.001; unpaired Student's t-test).

MANIO had p53-dependent anti-proliferative effect in colon carcinoma cells: The activity of the compound as wild-type p53 activator was studied in colon carcinoma cells with (HCT116 p53+/+) and without (HCT116 p53-/-) p53 (FIG. 3; Table 1). The $IC_{50}$ value of MANIO in HCT116 p53+/+ cells was about 50-fold lower than that obtained in HCT116 p53-/- cells, indicating a p53-dependent anti-proliferative effect. The known p53 activators CP-31398 and PRIMA-1MET (positive controls) demonstrated lower p53-dependence than the compound, since they presented similar IC50 values in HCT116 p53-/- cells (with a knocked out p53 pathway) (Table 1). In addition, CP-31398 and PRIMA-1MET presented highest IC50 values than MANIO in HCT116 p53+/+ cells, revealing a lower anti-proliferative effect on colon cancer cells than MANIO (Table 2). The marked inhibitory effect of MANIO on cell viability of colon cancer cells was further demonstrated by assessing the colony-forming ability (FIG. 4). Once again, MANIO was shown to reduce the colony-forming ability of HCT116 in a p53-dependent manner.

TABLE 1

$IC_{50}$ values obtained for MANIO, CP-31398 and PRIMA-$1^{MET}$ in colon carcinoma cells with (HCT116 p53$^{+/+}$) and without (HCT116 p53$^{-/-}$) p53.

| | $IC_{50}$ (µM) | |
| --- | --- | --- |
| | HCT116 p53$^{+/+}$ | HCT116 p53$^{-/-}$ |
| MANIO | 0.96 ± 0.04 | 48.25 ± 1.97*** |
| CP-31398 | 3.4 ± 0.1 | 7.3 ± 0.6** |
| PRIMA-$1^{MET}$ | 19.9 ± 4.0 | 13.1 ± 2.0 |

Cancer cells were plated at 5.0×103 cells/well in 96-well plates and incubated for 24 hours. Cells were then exposed to serial dilutions of MANIO, CP-31398 or PRIMA-1MET (from 0.3 to 80 µM). The effect of the compounds was analyzed following 48 hours incubation, using the sulforhodamine B (SRB) assay. The solvent DMSO corresponding to the maximum concentration used in these assays (0.025%) was included as control. Results are the mean±S.E.M. of 3-5 independent experiments. Value significantly different from HCT116 p53+/+(p<0.01, *p<0.001 unpaired Student's t-test).

Also the enantiomer (3R)-6,7-bis (hydroxymethyl)-1H, 3H-pyrrolo[1,2-c]thiazole presented relevant p53-dependent anti-proliferative activity (as revealed by the much lower $IC_{50}$ value in p53-expressing HCT116 cells compared to knockout p53 HCT116 cells, HCT116 p53−/−) (Table 2). The (3R) enantiomer also showed a high antiproliferative activity against several different types of cancer cells (Table 2). However, compared to MANIO, its cytotoxicity was shown to be smaller, particularly in colon cancer cells.

TABLE 2

$IC_{50}$ values of (3R)-6,7-bis(hydroxymethyl)-1H,3H-pyrrolo[1,2-c]thiazole in distinct human cancer cell lines.

|  | $IC_{50}$ (µM) |
|---|---|
| HCT116 p53+/+ (wt p53) | 5.11 ± 0.42 |
| HCT116 p53−/− (p53 null) | 51.83 ± 2.73 |
| MDA-MB-468 (mut p53 R273H) | 0.91 ± 0.0095 |
| SW837(mutp53 R248W) | 7.35 ± 0.89 |
| HT-29 (mutp53 R273H) | 5.88 ± 1.28 |
| Huh-7 (mutp53 Y220C) | 6.43 ± 0.32 |
| HepG2 (wtp53) | 50.3 ± 1.63 |
| H1299 (p53-null) | 25.5 ± 2.38 |
| H460 (wtp53) | 1.8 ± 0.089 |

Cancer cells were plated in 96-well plates and incubated for 24 hours. Cells were then exposed to serial dilutions of compound (from 0.3 to 80 µM). The effect of the compound was analyzed following 48 hours incubation, using the sulforhodamine B (SRB) assay. The solvent DMSO corresponding to the maximum concentration used in these assays (0.025%) was included as control. Results are the mean±S.E.M. of 3-5 independent experiments.

Both (3S)- and (3R)-6,7-bis (hydroxymethyl)-1H, 3H-pyrrolo[1,2-c]thiazoles presented significant anti-proliferative effect in different skin cancer cell lines (A375, SCC4925, A375C5 cells), with $IC_{50}$ values ranging from 25 to 35 µM.

Figure 5:
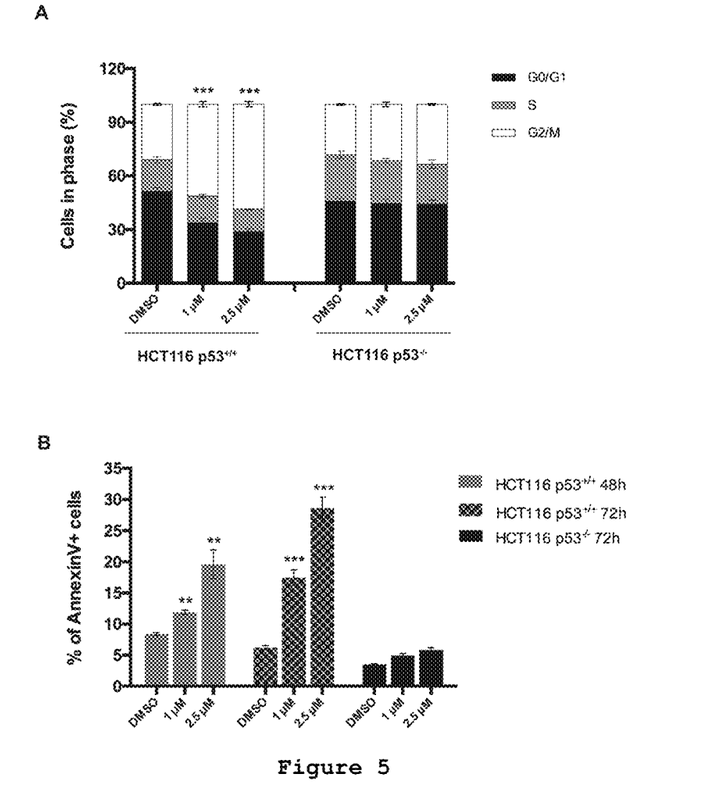
FIG. 5 illustrates the effect of 1 μM and 2.5 μM MANIO on cell cycle progression (A) and apoptosis (B) in HCT116 p53+/+ and HCT116 p53−/− cells. (A) Cell cycle phases were analysed by flow cytometry using propidium iodide (PI) and quantified using the FlowJo software, after 48 hours MANIO treatment. Data are mean±SEM (n=3; values significantly different from DMSO: *p<0.001; unpaired Student's t-test). (B) Apoptosis was analysed by flow cytometry using FITC-Annexin V and PI, after 48 hours or 72 hours MANIO treatment. Data are mean±SEM (n=3; values significantly different from DMSO: p<0.01; ***p<0.001; unpaired Student's t-test).

The compound MANIO induced p53-dependent cell cycle arrest and apoptosis in colon cancer cells: It was shown that the anti-proliferative effect of MANIO in HCT116 cells was associated with the induction of a G2/M-phase cell arrest (FIG. 5A), and of an apoptotic cell death (FIG. 5B), in a p53-dependent manner.

Figure 6:
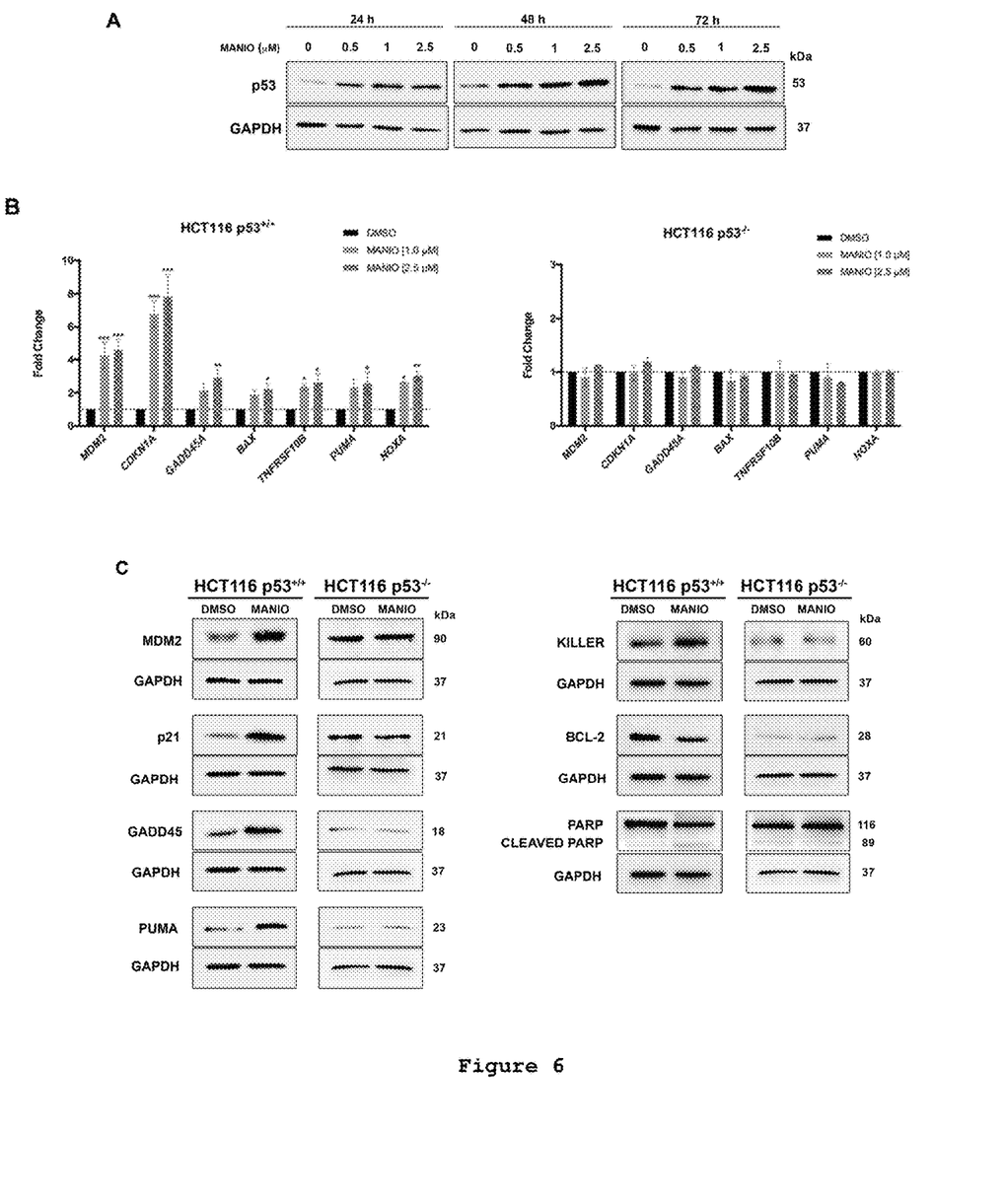

MANIO led to p53 stabilization and increased the mRNA and protein levels of p53 transcriptional targets in a p53-dependent manner in colon cancer cells: It was shown that 1 µM of MANIO increased the p53 protein levels (FIG. 6A), as well as of mRNA (FIG. 6B) and proteins (FIG. 6C) encoded by p53 target genes in HCT116 p53+/+, but not in HCT116 p53−/− cells. These results further support the induction of a p53-dependent effect by MANIO in colon carcinoma cells.

Figure 7:
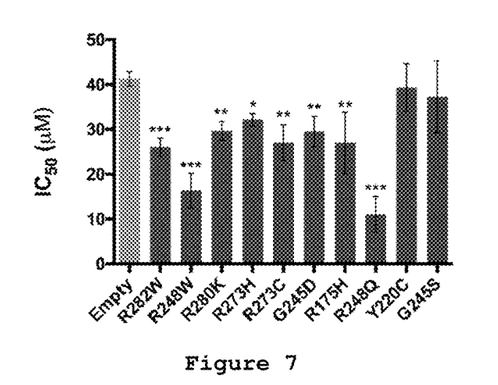
FIG. 7 illustrates the growth inhibitory effect of MANIO in mutant p53-transfected H1299 cells. H1299 cells were transfected with pcDNA3 plasmid expressing different p53 mutants (R282W, R248W, R280K, R273H, R273C, G245D, R175H, R248Q, Y220C, G245S), or with the empty pcDNA3 plasmid, using ScreenFect®A. The growth inhibitory effect was evaluated by sulforhodamine B assay after 48 hours treatment with MANIO. Data are mean±SEM (n=3-10; values significantly different from pcDNA3-Empty: *p<0.05 p<0.01; *p<0.001 unpaired Student's t-test).

MANIO reactivated mutant p53 forms ectopically expressed in p53-null cancer cells: MANIO was shown to reactivate different mutant p53 forms exogenously expressed in p53-null H1299 non-small cell lung cancer cells, particularly R282W, R248W, R280K, R273H, R273C, G245D, R175H and R248Q (FIG. 7). In opposition to cells transfected with the empty vector, the treatment of cells transfected with different p53 mutants with MANIO led to a significant growth inhibition (FIG. 7).

Figure 8:
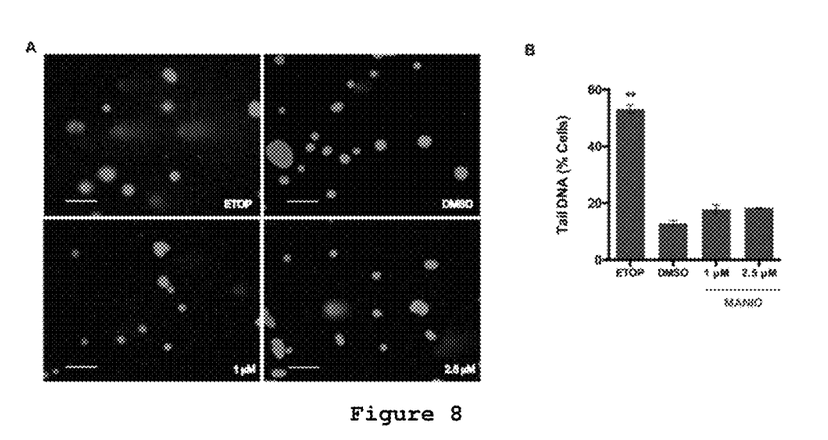
FIG. 8 illustrates the absence of genotoxicity of MANIO in HCT116 p53+/+ cells. In (A) DNA damage was measured by comet assay in HCT116 p53+/+ cells treated with 50 μM Etoposide (ETOP; positive control), MANIO or DMSO. Scale bar=20 μm; Magnification=200×. In (B), comet-positive cells (containing more than 5% of DNA in the tail; assessed by OPEN COMET/IMAGEJ) were quantified; 100 cells were analyzed in each group (n=3; values significantly different from DMSO: **p<0.01; unpaired Student's t-test).

MANIO is non-genotoxic in human colon cancer cells: Concerning the genotoxicity assays, the impact of two concentrations (1 and 2.5 µM) of MANIO in DNA damage was assessed in HCT116 p53+/+ cells. For that purpose, the Comet assay was used, which measures the ability of genotoxic agents to induce DNA strand breaks in eukaryotic cells. The results obtained showed that, unlike etoposide (ETOP; positive control), 1 and 2.5 µM of MANIO did not significantly increase the percentage of tail DNA (FIGS. 8A and B).

Figure 9:
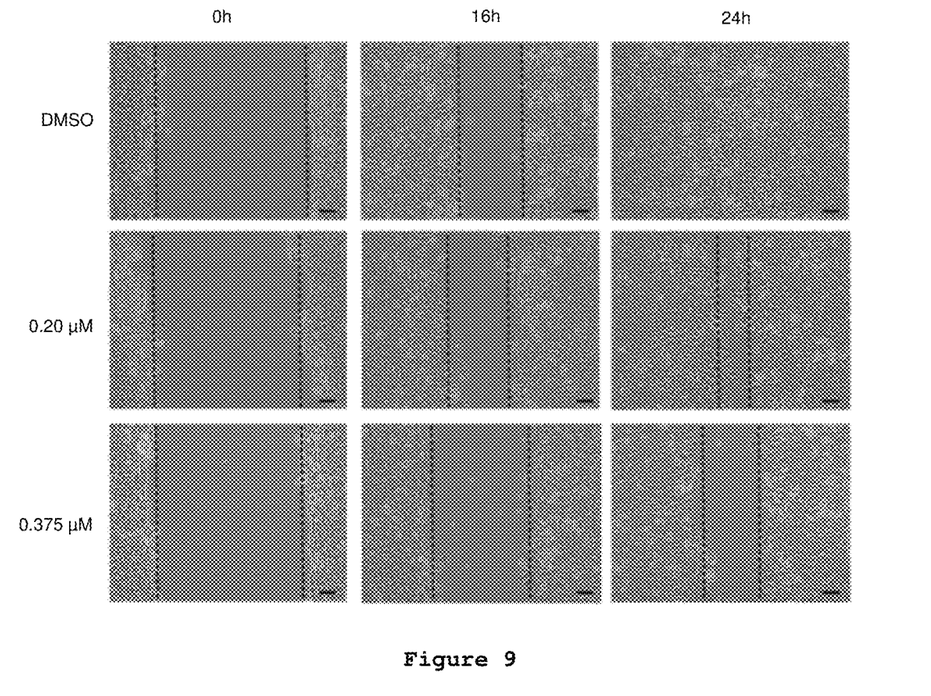
FIG. 9 illustrates the prevention of HCT116p53+/+ cell migration by MANIO. Confluent cells were treated with 0.20 and 0.375 μM MANIO or DMSO, and observed at different time-points in the wound healing assay (scale bar=50 μm and magnification=100×).

MANIO prevented cell migration of human colon cancer cells: The effect of MANIO on the migration ability of HCT116 p53+/+ cells was also studied. In the wound healing assay, for 0.2 and 0.375 µM (concentration with no significant effect on cell viability), MANIO significantly reduced the wound closure in HCT116 p53+/+ (FIG. 9).

Figure 10:
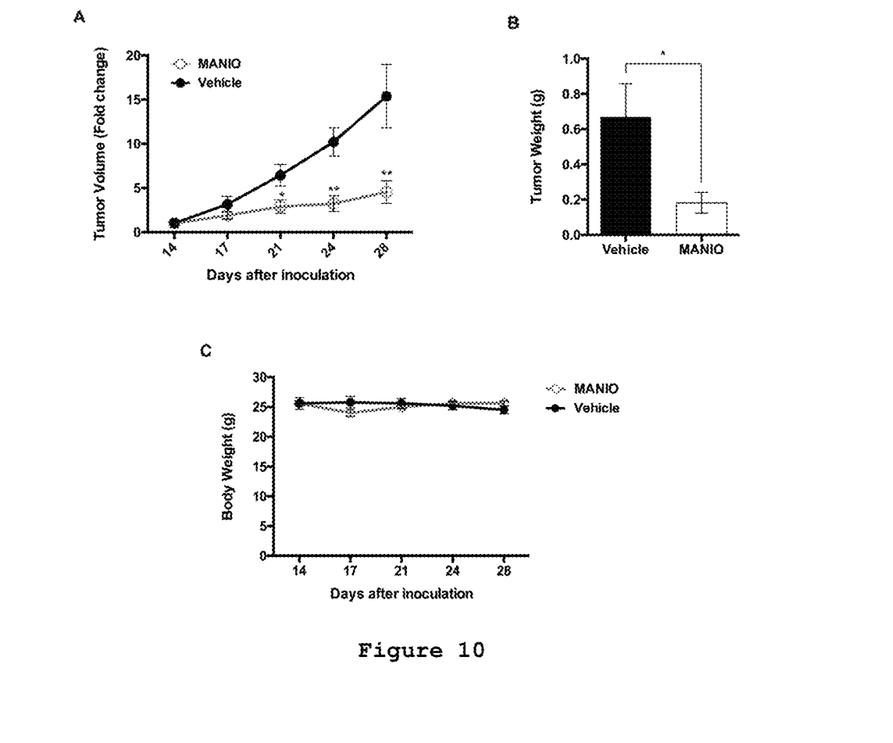

MANIO had antitumor activity in in vivo xenograft mouse models: In vivo studies using xenograft mice models showed that after four administrations of 100 mg/kg of MANIO, the growth of the HCT116 p53+/+ tumors was significantly inhibited when compared to vehicle administration (FIG. 10).

Although the preferred embodiments of the present invention have been disclosed for illustrative purposes, those skilled in the art will appreciate that various modifications, additions and substitutions are possible, without departing from the scope of the invention. Therefore, the present invention is not limited to the above-described embodiments, but the present invention is defined by the claims which follow, along with their fall scope of equivalents.

Lisbon, Apr. 29, 2019

The invention claimed is:

1. A method of treating cancer associated with wild-type or mutant p53 form comprising administering a composition comprising a compound or pharmaceutically acceptable salt of

(I)

wherein,
$R^1$=H;
$R^2$=phenyl;
$R^3$=methyl,
wherein the compound is a 3S enantiomer or a pharmaceutically acceptable salt thereof, to a patient in need thereof,
wherein the compound activates p53-dependent activity in wild-type p53 protein and/or reactivates p53-dependent activity in mutant p53 protein expressed in cancer cells by directly binding to the wild-type p53 protein and/or mutant p53 protein, and
wherein the cancer is selected from the group consisting of colorectal cancer, skin cancer, bladder cancer and lung cancer.

2. The method according to claim 1, wherein the cancer is colorectal cancer.

3. The method according to claim 1, wherein the cancer is skin, lung, and bladder cancer.

4. A method of treating cancer associated with wild-type or mutant p53 form comprising administering a pharmaceutical composition comprising a composition comprising a compound or pharmaceutically acceptable salt of (I)

wherein,
$R^1$=H;
$R^2$=phenyl;
$R^3$=methyl,
wherein the compound is a 3S enantiomer or a pharmaceutically acceptable salt thereof, to a patient in need thereof,
wherein the compound activates p53-dependent activity in wild-type p53 protein and/or reactivates p53-dependent activity in mutant p53 protein expressed in cancer cells by directly binding to the wild-type p53 protein and/or mutant p53 protein to a patient in need thereof, and
wherein the cancer is selected from the group consisting of colorectal cancer, skin cancer, bladder cancer and lung cancer.

5. The method according to claim 4, wherein the cancer is colorectal cancer.

6. The method according to claim 4, wherein the cancer is skin, lung, or bladder cancer.

7. The method according to claim 4, wherein the pharmaceutical composition is administered with a chemotherapeutic agent.

8. The method according to claim 4, wherein the pharmaceutical composition is administered via topical, oral, parenteral or injectable route.

9. The method according to claim 1, wherein the composition is administered via topical, oral, parenteral or injectable route.

* * * * *